United States Patent
Padilla Martinez et al.

(10) Patent No.: US 11,448,636 B2
(45) Date of Patent: Sep. 20, 2022

(54) MAGNETIC CHIP DETECTOR

(71) Applicant: PRATT & WHITNEY CANADA CORP., Longueuil (CA)

(72) Inventors: Alan Padilla Martinez, Montreal (CA); Pierre Castonguay, Sorel-Tracy (CA); Hubert Caron-Saint-Georges, Longueuil (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 0 days.

(21) Appl. No.: 17/036,683

(22) Filed: Sep. 29, 2020

(65) Prior Publication Data

US 2022/0099651 A1 Mar. 31, 2022

(51) Int. Cl.
*G01N 33/28* (2006.01)
*F02C 7/06* (2006.01)
*G01N 15/10* (2006.01)
*F01M 11/10* (2006.01)
*G01N 15/00* (2006.01)

(52) U.S. Cl.
CPC .......... *G01N 33/2858* (2013.01); *F02C 7/06* (2013.01); *G01N 15/1031* (2013.01); *F01M 11/10* (2013.01); *F05D 2220/323* (2013.01); *F05D 2260/98* (2013.01); *F05D 2270/11* (2013.01); *F16N 2200/04* (2013.01); *G01N 2015/0053* (2013.01)

(58) Field of Classification Search
CPC .......... G01N 33/2858; G01N 15/1031; G01N 2015/0053; F02C 7/06; F01M 11/10; F05D 2220/323; F05D 2260/98; F05D 2270/11; F16N 2200/04

USPC ........................................................ 324/204
See application file for complete search history.

(56) References Cited

U.S. PATENT DOCUMENTS

| | | | |
|---|---|---|---|
| 2,878,342 | A | 3/1959 | Arthur |
| 3,317,042 | A | 5/1967 | Botstiber |
| 3,432,750 | A | 3/1969 | Botstiber |
| 4,100,491 | A | 7/1978 | Newman, Jr. |

(Continued)

FOREIGN PATENT DOCUMENTS

| CN | 105298647 A | 2/2016 |
|---|---|---|
| EP | 0994337 A2 | 4/2000 |

(Continued)

OTHER PUBLICATIONS

Meggitt, Oil debris monitoring Chip Detector, https://meggittsensing.com/wp-content/uploads/2017/02/7-Datasheet-oildebris-monitoring-Detector-...pdf, accessed on Aug. 28, 2020.

(Continued)

*Primary Examiner* — Yi-Kai Wang
(74) *Attorney, Agent, or Firm* — Norton Rose Fulbright Canada LLP

(57) ABSTRACT

Magnetic chip detectors for detecting magnetic chips in a lubrication fluid are provided. The chip detector includes a first electric terminal, a second electric terminal and a magnet. The second electric terminal is spaced apart from the first electric terminal to define a gap between the first and second electric terminals. The gap exposes a cavity formed in the magnet for collecting magnetic chips. The cavity accommodates the accumulation of smaller and relatively harmless magnetic chips without triggering an alarm to reduce the occurrence of nuisance alarms.

20 Claims, 10 Drawing Sheets

(56) References Cited

U.S. PATENT DOCUMENTS

| | | |
|---|---|---|
| 5,406,208 A | 4/1995 | Bitts |
| 10,197,488 B2 | 2/2019 | Youssef |
| 10,317,354 B2 | 6/2019 | Ricci et al. |
| 2018/0031504 A1* | 2/2018 | Ricci ..................... G01N 27/06 |
| 2018/0275083 A1* | 9/2018 | Kiriyama .............. G01N 27/12 |

FOREIGN PATENT DOCUMENTS

| | | |
|---|---|---|
| EP | 3279650 A1 | 2/2018 |
| GB | 2029580 A | 3/1980 |

OTHER PUBLICATIONS

Eaton, Aerospace Sensing & Controls Chip Detectors, https://www.herberaircraft.com/pdf/Glenolden/Chip%20Detectors.pdf, accessed on Aug. 28, 2020.

Eaton Aerospace Group, Oil Debris Monitoring in Aerospace Engines and Helicopter Gearboxes, Mid-Atlantic Symposium on Aerospace, Unmanned Systems and Rotorcraft, Apr. 10, 2014, Radnor, PA, United States.

European Patent Office, Communication of extended European search report for European patent application No. 21199994.1, dated Feb. 22, 2022.

\* cited by examiner

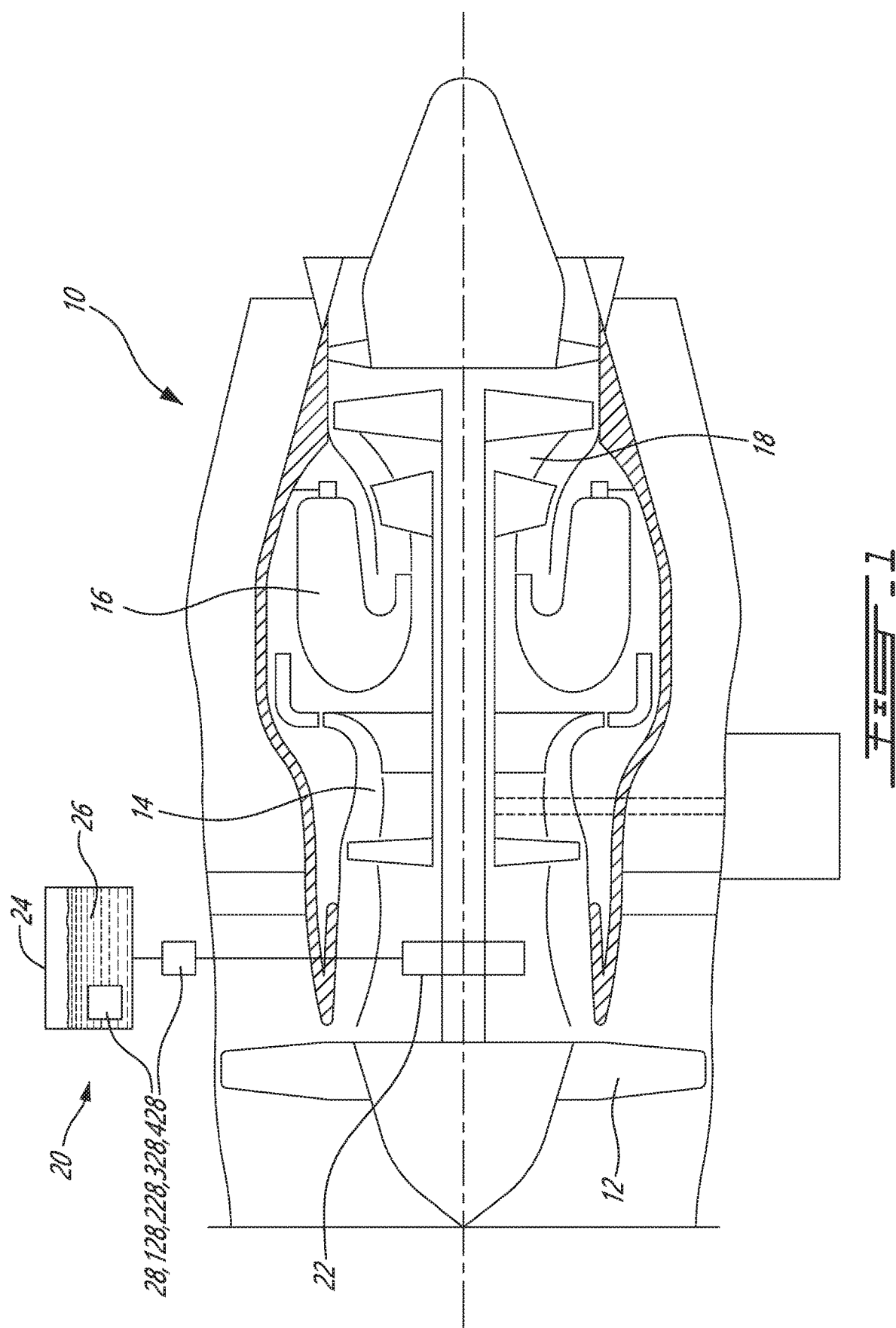

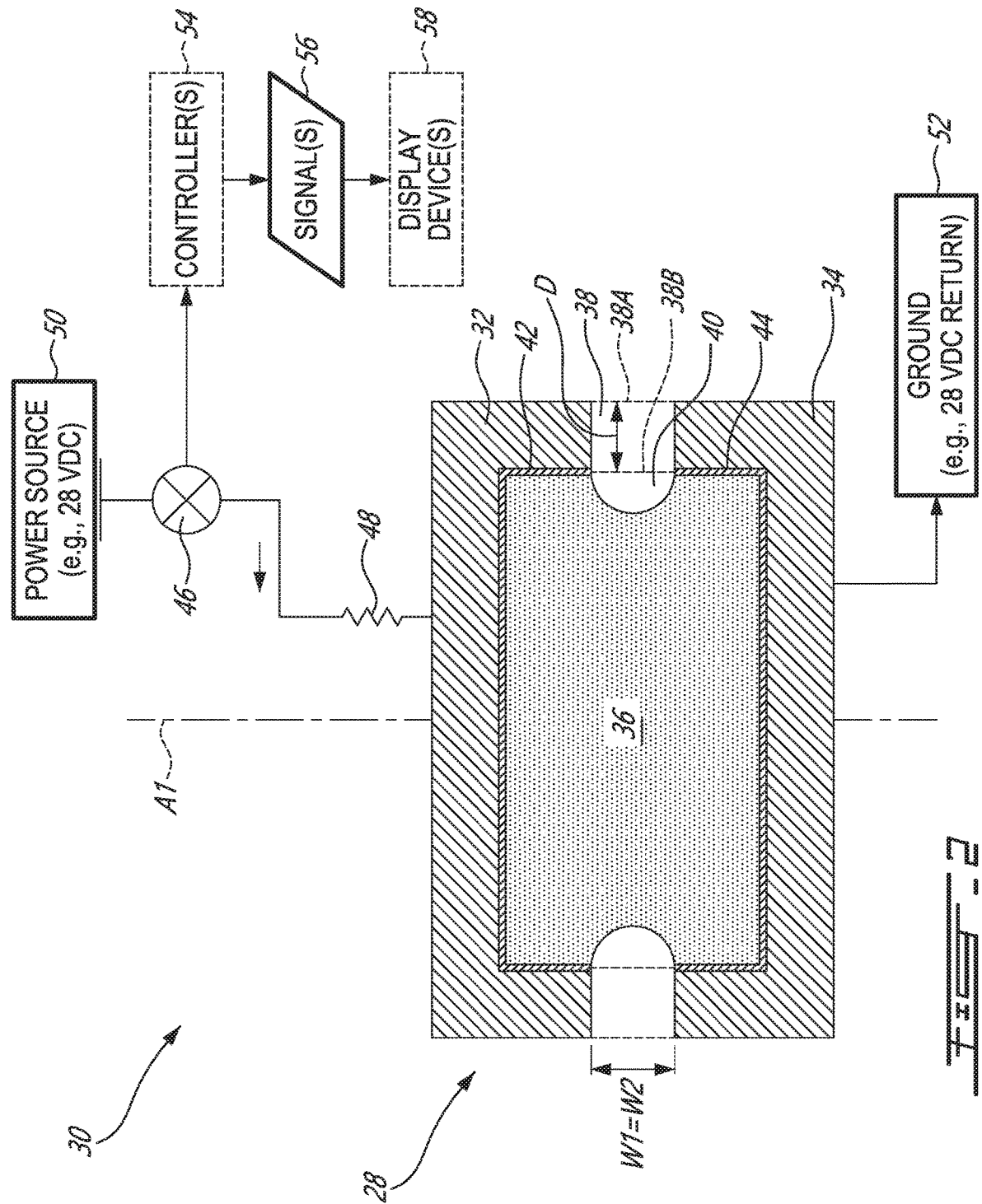

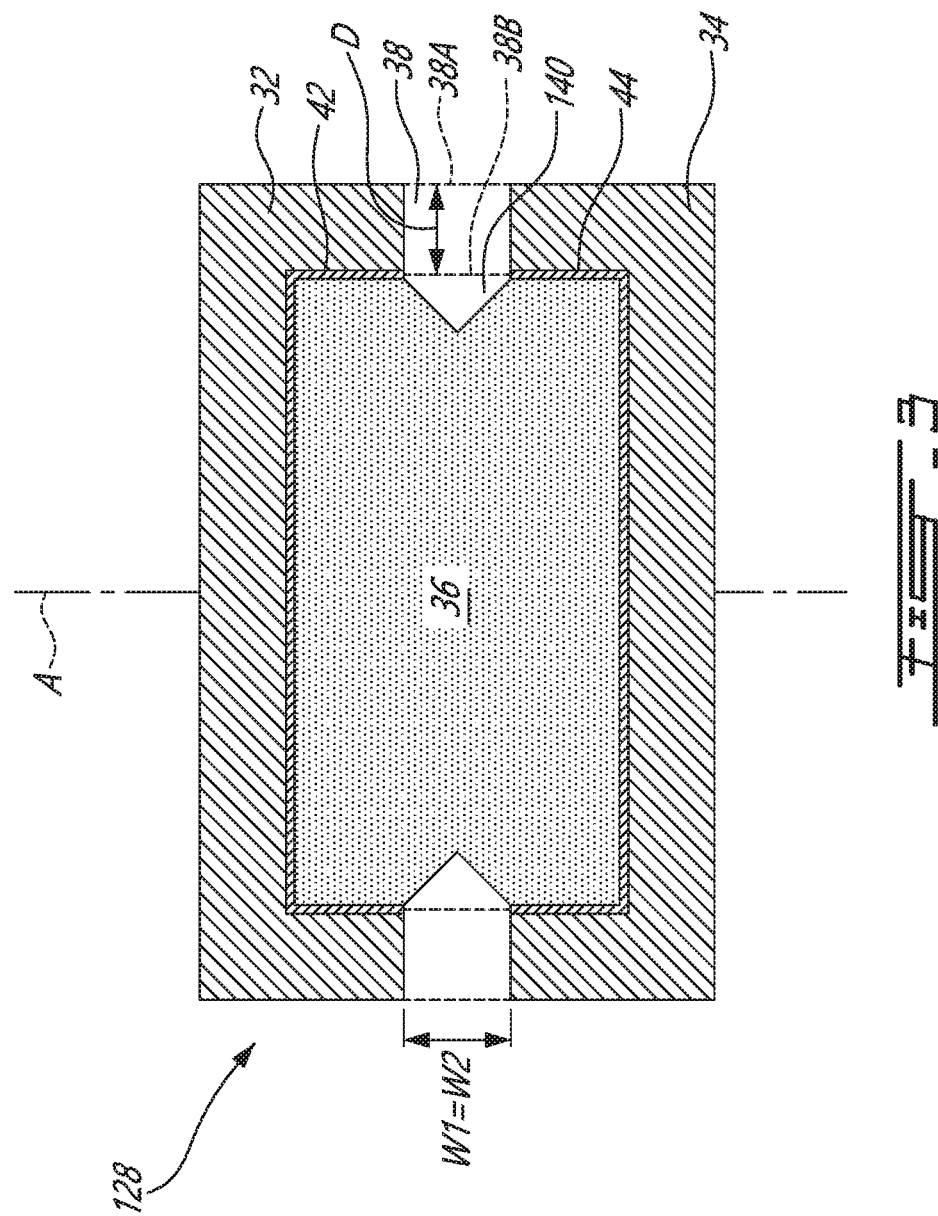

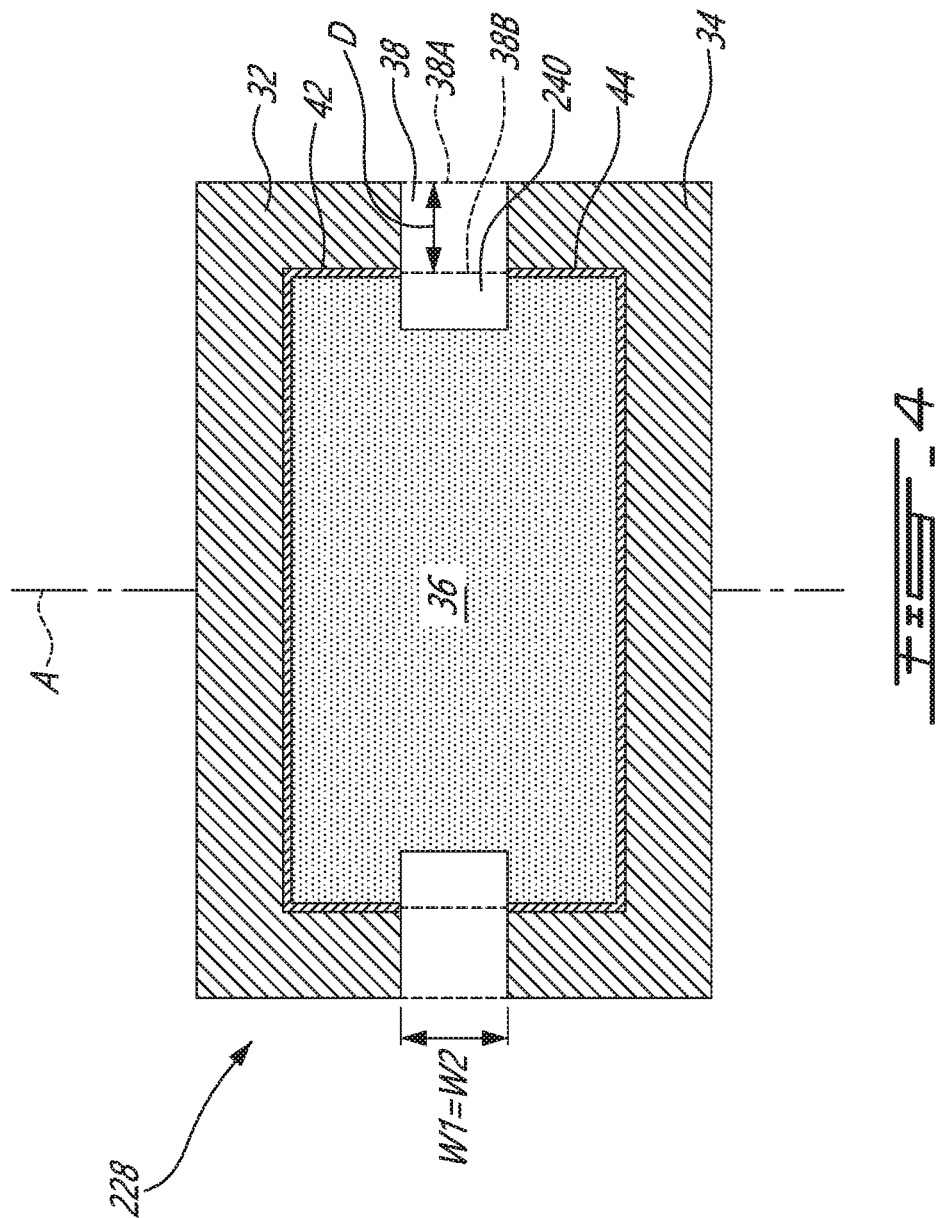

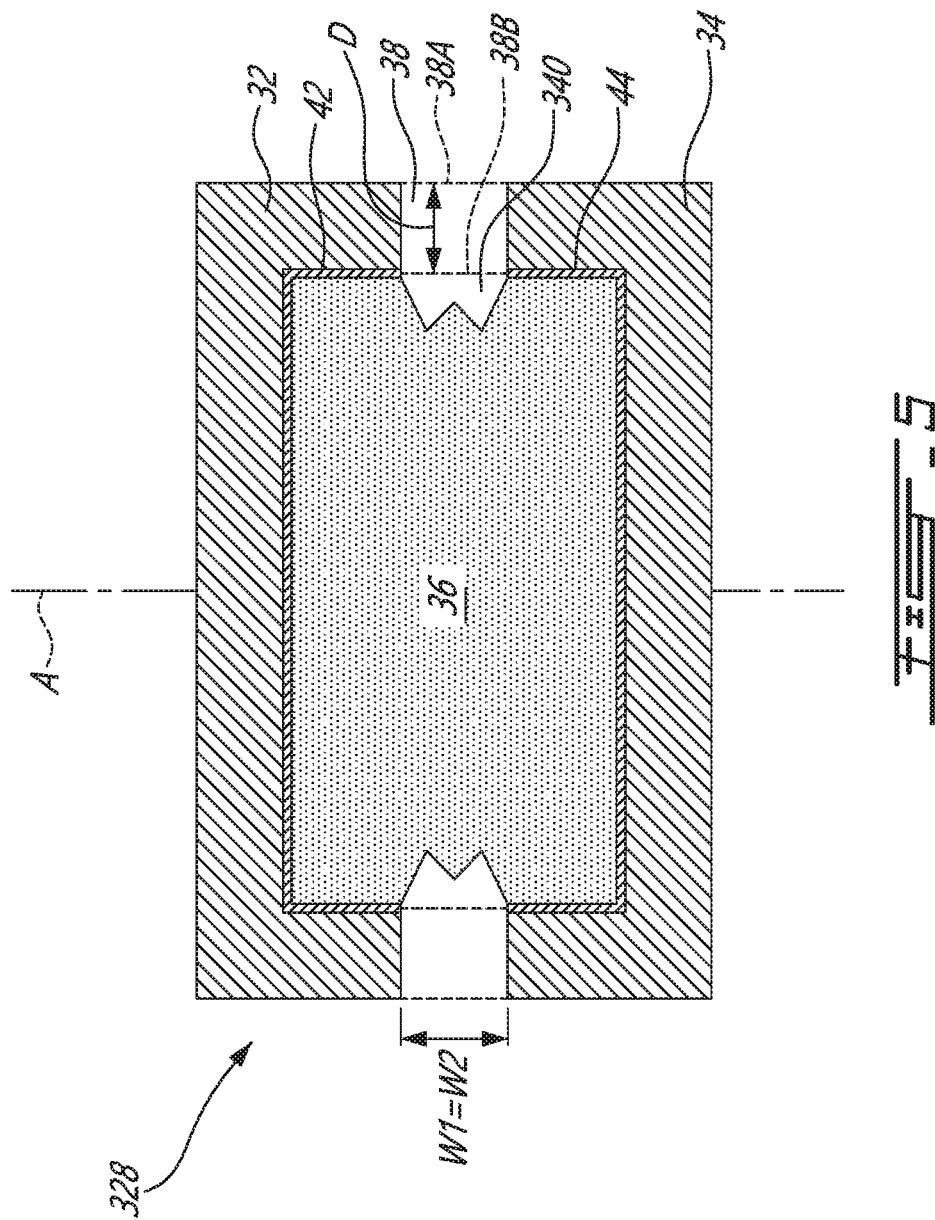

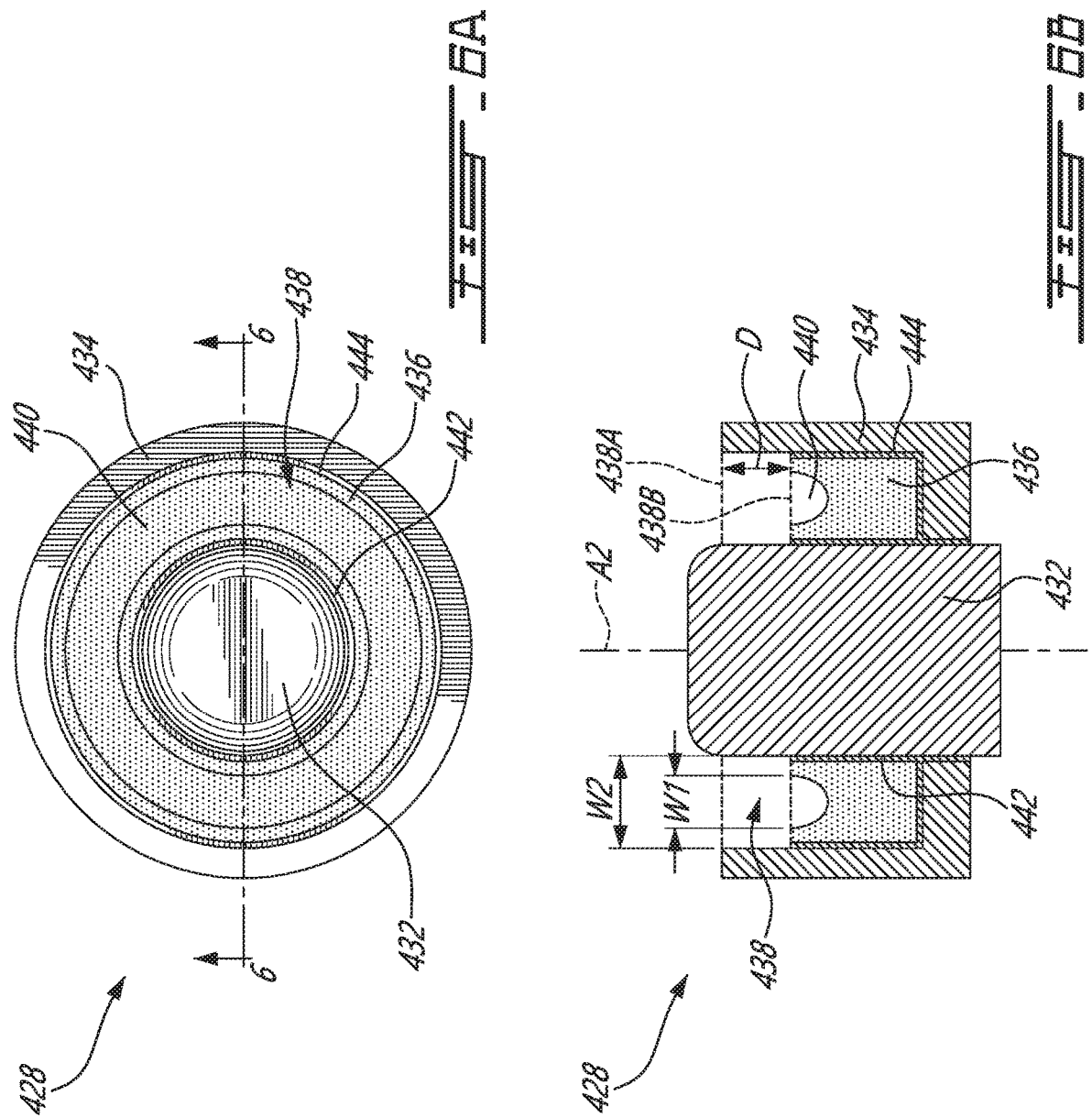

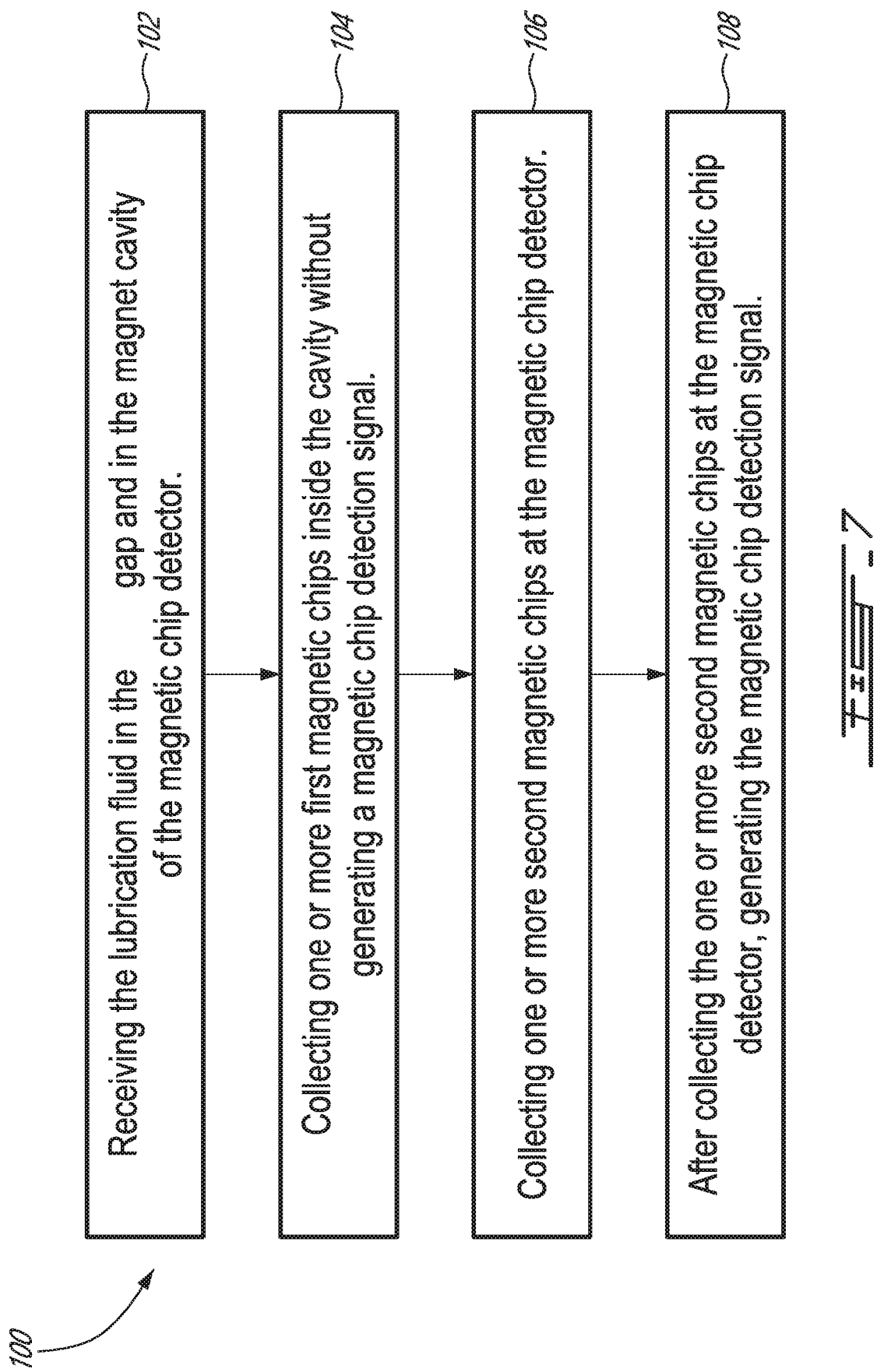

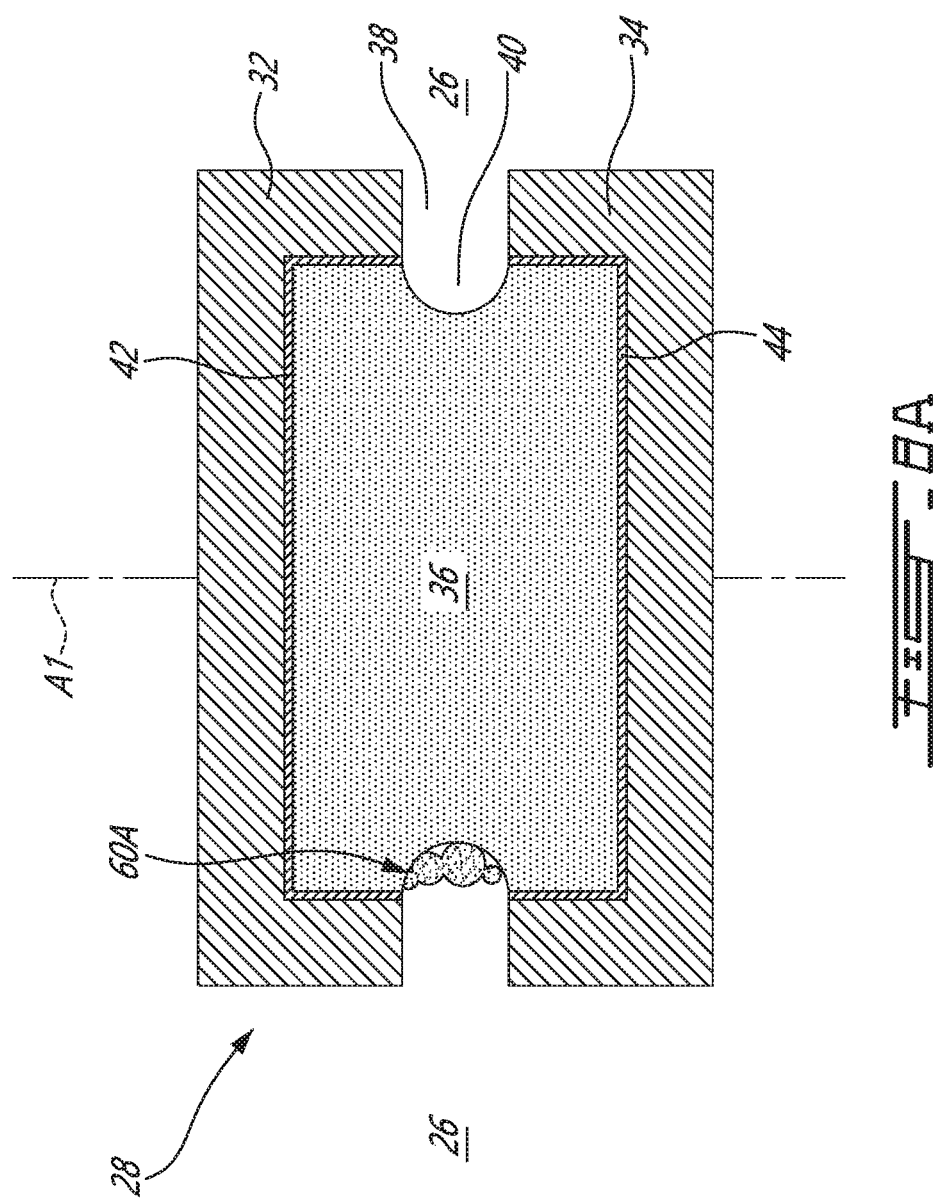

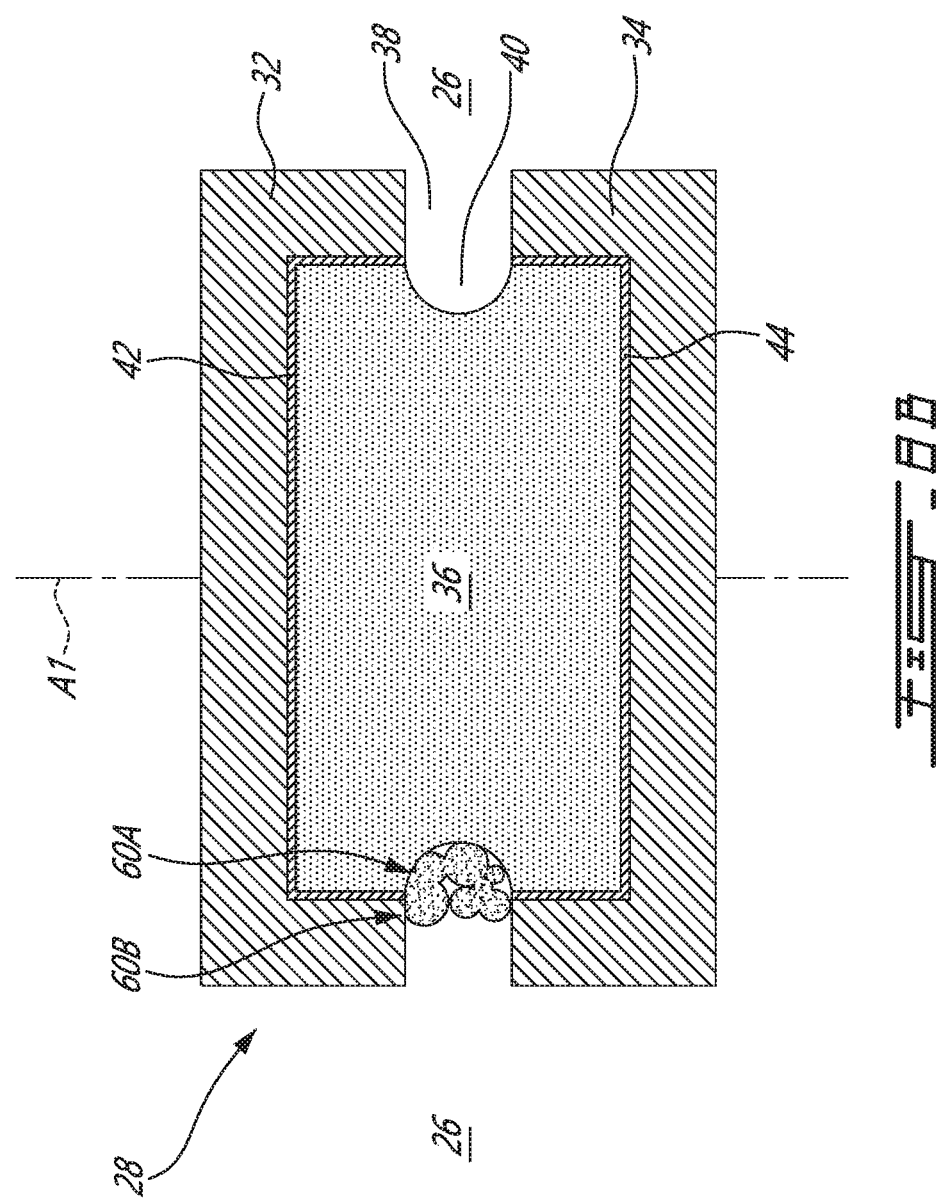

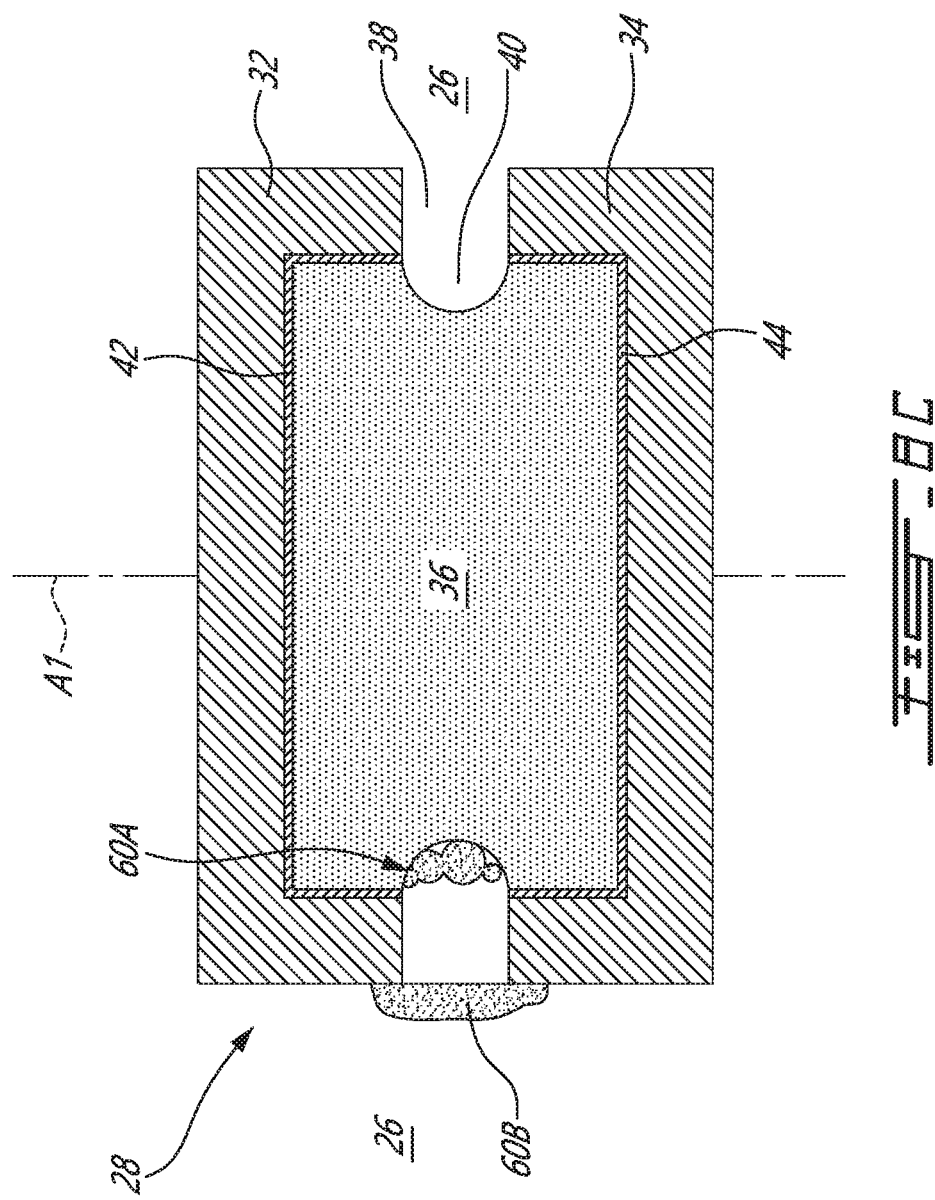

MAGNETIC CHIP DETECTOR

TECHNICAL FIELD

The disclosure relates generally to health monitoring of aircraft engines, and more particularly to the detection of magnetic chips in lubrication fluids of aircraft engines.

BACKGROUND

A magnetic chip detector is commonly found in a lubrication system of an aircraft engine to assess the presence of magnetic chips in the lubrication fluid. The chip detector is immersed in the lubrication fluid so as to be exposed to the magnetic chips carried by the lubrication fluid. The presence of magnetic chips in the lubrication fluid may indicate a developing and/or impending mechanical problem exhibiting excessive wear of one or more components of the aircraft engine interacting with the lubrication system. The chip detector includes a magnet that attracts and retains the magnetic chips. When magnetic chips are collected by the chip detector, a gap between two electric terminals is eventually bridged so as to provide electric continuity and cause an indication (e.g., alarm) to be provided to an operator of the aircraft so that an appropriate action can be taken if necessary.

Some magnetic chip detectors are prone to generate false detections. Such false detections can be a nuisance by unnecessarily alarming an aircraft operator and potentially causing flight delays or cancellations. Improvement is desirable.

SUMMARY

In one aspect, the disclosure describes a magnetic chip detector comprising:

a first electric terminal;

a second electric terminal spaced apart from the first electric terminal to define a gap therebetween, the gap having a width between the first and second electric terminals and a depth between a first side and a second side of the gap, the first side of the gap defining an opening for establishing fluid communication between the gap and an ambient environment; and a magnet disposed outside of the gap and adjacent the second side of the gap, the magnet including a recess defining a cavity in fluid communication with the gap to collect one or more magnetic chips that have entered the gap via the opening.

In another aspect, the disclosure describes an aircraft engine comprising:

a lubrication system for distributing lubrication fluid to one or more lubrication loads; and a magnetic chip detector immersed in the lubrication fluid, the magnetic chip detector comprising:

a first electric terminal;

a second electric terminal spaced apart from the first electric terminal to define a gap therebetween, the gap having a width between the first and second electric terminals and a depth between a first side and a second side of the gap, the first side of the gap defining an opening for establishing fluid communication between the gap and an ambient environment; and a magnet disposed outside of the gap, the magnet including a groove formed therein, the groove being disposed adjacent the second side of the gap and in fluid communication with the gap via the second side of the gap.

In a further aspect, the disclosure describes a method of detecting one or more magnetic chips in a lubrication fluid of an engine using a magnetic chip detector including: a first electric terminal and a second electric terminal defining a gap therebetween; and a magnet including a magnet cavity adjacent the gap, the method comprising:

receiving the lubrication fluid in the gap and in the magnet cavity;

collecting one or more first magnetic chips inside the magnet cavity without generating a magnetic chip detection signal;

collecting one or more second magnetic chips at the magnetic chip detector; and after collecting the one or more second magnetic chips at the magnetic chip detector, generating the magnetic chip detection signal.

Further details of these and other aspects of the subject matter of this application will be apparent from the detailed description included below and the drawings.

DESCRIPTION OF THE DRAWINGS

Reference is now made to the accompanying drawings, in which:

FIG. 1 is a schematic axial cross-section view of a turbofan gas turbine engine including one or more magnetic chip detectors as described herein;

FIG. 2 is a schematic illustration of an exemplary axial gap magnetic chip detector integrated into a chip detection circuit;

FIG. 3 is a schematic illustration of another exemplary axial gap magnetic chip detector;

FIG. 4 is a schematic illustration of another exemplary axial gap magnetic chip detector;

FIG. 5 is a schematic illustration of another exemplary axial gap magnetic chip detector;

FIG. 6A is a schematic end-on view of an exemplary radial gap magnetic chip detector;

FIG. 6B is a schematic axial cross-section view of the radial gap magnetic chip detector taken along line 6-6 of FIG. 6A;

FIG. 7 is a flowchart of an exemplary method of detecting one or more magnetic chips in a lubrication fluid of an aircraft engine;

FIG. 8A is a schematic illustration of the magnetic chip detector of FIG. 2 with smaller chips accumulated in a recess formed in a magnet of the magnetic chip detector;

FIG. 8B is a schematic illustration of the magnetic chip detector of FIG. 2 with smaller chips accumulated in a recess and also bridging a gap between two electric terminals of the magnetic chip detector; and FIG. 8C is a schematic illustration of the magnetic chip detector of FIG. 2 with small particles accumulated in the recess and a large particle bridging a gap between the two electric terminals of the magnetic chip detector.

DETAILED DESCRIPTION

The following description discloses magnetic chip detectors, associated aircraft systems and circuits, and methods. In some embodiments, a magnetic chip detector as described herein may help reduce a frequency of or eliminate the occurrence of nuisance detections (e.g., alarms) associated with the accumulation of acceptable smaller magnetic chips (e.g., fine ferromagnetic debris/particles) at the magnetic chip detector.

Some smaller magnetic chips can be generated during the normal operation of the aircraft engine and may not necessarily be indicative of a developing or impending mechanical problem. For example, such smaller magnetic chips can normally be generated during the initial period (e.g., a few hundred hours) of operation of an aircraft engine following initial entry into service or following extensive maintenance such as an overhaul. This initial period is also known as the engine's "break-in" period. Detections caused by the accumulation of the acceptable smaller magnetic chips, during the break-in period for example, oppose the design intent of the magnetic chip detector and are undesirable since they do not provide an accurate indication of a possible developing or impending problem. In some embodiments, the magnetic chip detectors described herein may accommodate some accumulation of such smaller magnetic chips while also reducing or eliminating the occurrence of nuisance detections that may occur during the initial operating period of an aircraft engine for example.

The term "substantially" as used herein may be applied to modify any quantitative representation which could permissibly vary without resulting in a change in the basic function to which it is related.

Aspects of various embodiments are described through reference to the drawings.

FIG. 1 is a schematic axial cross-section view of aircraft engine 10 of a (e.g., turbofan gas turbine engine) type preferably provided for use in subsonic flight, generally comprising, in serial flow communication, fan 12 through which ambient air is propelled, multistage compressor 14 for pressurizing the air, combustor 16 in which the compressed air is mixed with fuel and ignited for generating an annular stream of hot combustion gases, and turbine section 18 for extracting energy from the combustion gases. Engine 10 may be mounted to an aircraft and used to propel such aircraft. Engine 10 may include lubrication system 20 shown schematically and partially in FIG. 1. Lubrication system 20 may serve to lubricate, cool and clean one or more lubrication loads 22 such as bearings and gears of engine 10.

Lubrication system 20 may include tank 24 and other components such as one or more pumps, one or more valves, and one or more filters. Tank 24 may be a reservoir containing a supply of lubrication fluid 26 such as oil for use by lubrication system 20. Lubrication system 20 may include one or more magnetic chip detectors (MCDs) 28, 128, 228, 328, 428 as described herein. For example, lubrication system 20 may include a single MCD 28, 128, 228, 328, 428 or a plurality of MCDs 28, 128, 228, 328, 428 disposed at different locations within lubrication system 20. MCD 28, 128, 228, 328, 428 may be at least partially immersed in lubrication fluid 26 during operation. For example, MCD 28, 128, 228, 328, 428 be disposed inside tank 24, inside a gearbox, or in a scavenge line.

FIG. 2 is a schematic illustration of an exemplary MCD 28 integrated into a chip detection circuit 30 of engine 10. In some embodiments, MCD 28 may be an axial gap MCD 28, which may, in some embodiments, also be called a "disk type" magnetic chip detector or a magnetic plug with an axial chip gap 38. Alternatively, a radial gap MCD such as MCD 428 shown in FIGS. 6A, 6B may be integrated into chip detection circuit 30 of engine 10. MCD 28 may include first electric terminal 32, second electric terminal 34 and magnet 36. First electric terminal 32 and second electric terminal 34 may also be referred to as pole pieces or electric contacts of MCD 28. It is understood that the use of MCD 28 is not limited to aircraft engines. MCD 28 may be used in lubrication system of various applications, such as pumps, power-generation and automotive, that may be sensitive to metal contamination.

Second electric terminal 34 may be spaced apart from first electric terminal 32 along axis A1 to define gap 38 between first electric terminal 32 and second electric terminal 34. Gap 38 may have an outer lateral side 38A and an opposite inner lateral side 38B. Outer lateral side 38A may be facing and define an opening to the ambient environment surrounding MCD 28 and may provide fluid communication between gap 38 and the ambient environment so that the lubrication fluid 26 may enter and exit gap 38. Inner lateral side 38B of gap 38 may be laterally opposed to outer lateral side 38B relative to axis A1.

As shown in FIG. 2, first and second terminals 32, 34 may be cylindrically shaped and gap 38 may extend around axis A1. Outer lateral side 38A may be disposed radially-outwardly of inner lateral side 38B in relation to axis A1. FIG. 2 shows a schematic axial cross-section of MCD 28 in a plane that is parallel to and which contains axis A1. First electric terminal 32 and second electric terminal 34 may extend partially or substantially completely (i.e., circumferentially) around axis A1. Similarly, gap 38 may also extend partially or substantially completely (i.e., circumferentially) around axis A1. In some embodiments, first electric terminal 32 and second electric terminal 34 may have a substantially circular cross-sectional profile taken transversely to axis A1 (i.e., when viewed along axis A1). In such embodiments, gap 38 may be ring-shaped (e.g., annular) and define an annulus centered about axis A1. It is understood that first electric terminal 32, second electric terminal 34 and magnet 36 may have a cross-sectional profile of another shape. For example, aspects of the present disclosure may be applied to magnetic chip detectors of various shapes including square or rectangular terminals defining a four-sided axial gap, or, terminals shaped provide a one-sided gap. Aspects of the present disclosure may also be applied to magnetic chip detectors of the radial gap type as explained below.

Magnet 36 may be disposed laterally (e.g., radially) inwardly of gap 38. Magnet 36 may include a recess defining cavity 40 in fluid communication with gap 38 via inner lateral side 38B of gap 38. Cavity 40 may extend partially or substantially completely around axis A1. Cavity 40 may be in substantial axial alignment with gap 38. Cavity 40 may be adjacent to gap 38. A radially outer side of cavity 40 may be open to gap 38. In some embodiments, a volume defined by cavity 40 may be substantially contiguous with a volume defined be gap 38 so as to define a radially inner extension to gap 38. Cavity 40 may be laterally and/or radially offset from gap 38. Magnet 36 may also have a substantially circular cross-sectional profile taken transversely to axis A1 (i.e., when viewed along axis A1). In such embodiments, cavity 40 may be ring-shaped (e.g., annular) and define an annulus centered about axis A1. The presence of gap 38 between first and second electric terminals 32, 34 may expose cavity 40 of magnet 36 to the ambient environment which contains lubrication fluid 26 during operation. In some embodiments, first electric terminal 32, second electric terminal 34 and magnet 36 may be (but not necessarily) axisymmetric about axis A1.

In some embodiments, the recess defining cavity 40 may include a groove formed into magnet 36 and having a substantially U-shaped transverse cross-sectional profile. It is understood that the recess may have a cross-sectional profile of another shape. In other words, the recess may include a track or channel of any suitable shape that is formed in a radially outer surface of magnet 36. Cavity 40 may be formed into the initial shape of magnet 36 during casting of magnet 36 for example. Grinding and/or machining may be used to form cavity 40 into magnet 36.

Cavity 40 may have cavity width W1 along axis A1. Gap 38 may have gap width W2 along axis A1. In some embodiments, cavity width W1 and gap width W2 may be substantially equal. However, it is understood that cavity width W1 and gap width W2 may be different for different applications depending on the type(s) and/or target size(s) of magnetic chips to be detected and the selected shapes, sizes and/or volumes of gap 38 and of cavity 40. Gap 38 may have a depth D transverse to axis A1 and extending between outer lateral side 38A and inner lateral side 38B of gap 38.

In some embodiments, magnet 36 may be disposed (e.g., sandwiched) axially between first and second terminals 32, 34. For example, first electric terminal 32 may be cup-shaped and define a first receptacle in which a first (e.g., axial) portion of magnet 36 is received and suitably retained. Second electric terminal 34 may also be cup-shaped and define a second receptacle in which a second (e.g., axial) portion of magnet 36 is received and suitably retained. First electric terminal 32 and second electric terminal 34 may form a partial housing for magnet 36. First electric terminal 32 and second electric terminal 34 may be made from a suitable electrically conductive (e.g., metallic) material. Magnet 36 may be cylindrical-shaped with a circumferential cavity 40 formed therein.

The integration of first electric terminal 32, second electric terminal 34 and magnet 36 may provide for little or no electric continuity being initially provided between first electric terminal 32 and second electric terminal 34. In other words, gap 38 may cause chip detection circuit 30 to initially be in a substantially open-circuit state. A suitable first electric insulator 42 may be operatively disposed between first electric terminal 32 and magnet 36. In some embodiments, a suitable second electric insulator 44 may be operatively disposed between second electric terminal 34 and magnet 36. Electric insulators 42, 44 may include a liner made from a suitable relatively electrically insulating (e.g., polymeric) material.

The detection of magnetic chips may be achieved by one or more magnetic chips bridging gap 38 and establishing the electric continuity between first electric terminal 32 and second electric terminal 34 via the collected magnetic chip(s). Electric bridging between first electric terminal 32 and second electric terminal 34 across gap 38 may reduce the electric resistance between first electric terminal 32 and second electric terminal 34.

MCD 28 may be part of chip detection circuit 30 of engine 10 and may be used for health monitoring of engine 10 to detect a possible developing or impending mechanical problem with engine 10. Although FIG. 1 illustrates engine 10 as a turbofan gas turbine engine, MCD 28 may be incorporated into any type of aircraft engine (e.g., turboprop engine or turboshaft engine) requiring lubrication fluid 26. Engine 10 may be mounted to any type of aircraft such as a fixed-wing aircraft or a rotary-wing aircraft.

Chip detection circuit 30 may include MCD 28, sensor 46 and resistor 48 electrically connected in series between power source 50 and ground 52, which may be a return path ground. In some embodiments, power source 50 may be a direct current (DC) voltage source (e.g., 28 Volts DC) and ground 52 may be a (e.g., 28 Volts DC) return path ground. Sensor 46 may be configured to detect a current i through circuit 30. In some embodiments, sensor 46 may include a Hall effect sensor for example. In various embodiments, sensor 46 may be of any type (e.g., electric current sensor) suitable to detect the reduced electric resistance (i.e., increase or onset of electric continuity) across first and second terminals 32, 34.

During operation of MCD 28, the presence of one or more magnetic chips collected at MCD 28 by way of the attraction of the magnetic chips to magnet 36 may cause gap 38 to become electrically bridged so that the initial open-circuit state of chip detection circuit 30 may become closed by electric continuity across gap 38 established by the one or more magnetic chips. The metallic chips may also be ferromagnetic and electrically conductive. The closing of chip detection circuit 30 may be accompanied by a reduced electric resistance across first and second terminals 32, 34, and consequently cause an increase in current i delivered through chip detection circuit 30. Such increase in current i may be detected by way of sensor 46 and indicative of a legitimate magnetic chip detection indicative of a developing or impending mechanical problem. A suitable threshold increase in electric current i and/or a threshold magnitude of electric current i may be correlated to a legitimate magnetic chip detection and used by optional controller 54 to cause an indication to be produced. For example, controller 54 may substantially continuously or periodically compare an actual measured value of the current i with a stored predetermined threshold value. Alternatively, sensor 46 may comprise a transducer configured to output magnetic chip detection signal 56 directly and only when the detected current i is indicative of a legitimate magnetic chip detection.

In response to the magnetic chip detection, a suitable indication (e.g., alarm) may be provided to an operator (e.g., flight crew) of the aircraft so that suitable remedial action may be carried out. Such remedial action may include safely landing the aircraft at the next available opportunity. Other remedial actions may include troubleshooting and/or one or more maintenance tasks.

Sensor 46 may be operatively connected to a suitable alarm device of the aircraft. Sensor 46 may also be operatively connected to controller 54. Magnetic chip detection signal 56 may be generated by controller 54 based on input (e.g., indicative of an actual value of current i) from sensor 46. In response to sensor 46 detecting a legitimate magnetic chip detection, one or more magnetic chip detection signal(s) 56 may be generated so that optional display device 58 may be caused to provide a suitable indication to the operator of the aircraft. In some embodiments, controller 54 may be of the type sometimes referred to as an electronic engine controller (EEC), which may be part of a full authority digital computer (or electronics) control (FADEC). A FADEC may include controller 54 and related accessories that control various aspects of performance of aircraft engine 10. Controller 54 may include one or more digital computers or other data processor(s) and non-transitory computer readable medium(ia) (i.e., memory) having computer readable program code (i.e., instructions) embodied thereon. Such program code may be executed entirely or in part by controller 54 or other data processing device(s).

The indication provided to the operator of the aircraft may include a visual indication displayed on display device 58 (e.g., indicator light, liquid crystal display (LCD), plasma display, light-emitting diode (LED) based display) in a cockpit of the aircraft for example. Display devices 58 may be part of a crew alerting system (CAS) of the aircraft. In various embodiments, the indication may include a visual and/or aural indication.

FIGS. 3-5 are schematic axial cross-sections of other exemplary axial gap MCDs 128, 228 and 338 respectively. MCDs 128, 228 and 338 are generally similar to MCD 28 except for having cavities 140, 240 and 340 of different shapes. Like elements are identified using like reference numerals between different MCDs 28, 128, 228 and 338. In reference to FIG. 3, cavity 140 of MCD 128 may have a substantially V-shaped cross-sectional profile. In reference to FIG. 4, cavity 240 of MCD 228 may have a square or rectangular cross-sectional profile. In reference to FIG. 5, cavity 340 of MCD 328 may have a substantially W-shaped cross-sectional profile. It is understood that cavities of various shapes may be suitable for use in the MCDs described herein in various applications.

FIG. 6A is a schematic end-on view (along axis A2) of an exemplary radial gap MCD 428 and FIG. 6B is a schematic axial cross-section view of the radial gap MCD 428. The principle of operation of MCD 428 may be generally similar to the principle of operation of MCD 28 described above. MCD 428 may be integrated into chip detection circuit 30 in the same manner as MCD 28. MCD 428 may include first electric terminal 432, second electric terminal 434 spaced apart from first electric terminal 432 to define gap 438 therebetween, and magnet 436 disposed outside of gap 438. Gap 438 may be a radial gap disposed between first electric terminal 432 and second electric terminal 434. For example, first and second electric terminals 432, 434 may be radially spaced apart relative to axis A2. Gap 438 may have width W2 between first and second electric terminals 432, 434 and depth D between axially outer side 438A and axially inner side 438B of gap 438. Axially outer side 438A of gap 438 may define an opening for establishing fluid communication between gap 438 and an ambient environment.

Magnet 436 may have an annular shape and may be disposed adjacent axially inner side 438B of gap 438. Magnet 436 may include a recess defining cavity 440 in fluid communication with gap 438 to collect one or more magnetic chips that have entered gap 438 via the opening defined by axially outer side 438A of gap 438. In some embodiments, gap 438 and cavity 440 may extend substantially completely around axis A2 or partially around axis A2.

Cavity 440 may be disposed adjacent to gap 438. Cavity 440 may be disposed substantial radial alignment with gap 438. In some embodiments, width W1 of cavity 440 may be substantially equal to width W2 of gap 438. In some embodiments, width W1 of cavity 440 may be less than width W2 of gap 438. Cavity 440 may have any suitable cross-sectional shape including U-shaped, V-shaped, W-shaped and square/rectangular.

A suitable first electric insulator 442 may be operatively disposed between first electric terminal 432 and magnet 436. A suitable second electric insulator 444 may be operatively disposed between second electric terminal 434 and magnet 436.

FIG. 7 is a flowchart of an exemplary method 100 for detecting one or more magnetic chips in lubrication fluid 26 of aircraft engine 10 or other type of engine. Method 100 is described below in relation to MCD 28 but it is understood that method 100 may be performed using any of MCDs 28, 128, 228, 328, 428 and chip detection circuit 30 described herein. In various embodiments, method 100 may include:

receiving lubrication fluid 26 in gap 38 and in cavity 40 of MCD 28 (see block 102);

collecting one or more first magnetic chips 60A (shown in FIG. 8A) inside cavity 40 without generating the magnetic chip detection signal 56 (shown in FIG. 2) (see block 104);

collecting one or more second magnetic chips 60B (shown in FIGS. 8B and 8C) at MCD 28 (see block 106); and after collecting the one or more second magnetic chips 60B at MCD 28, generating the magnetic chip detection signal 56 (shown in FIG. 2) (see block 108).

FIGS. 8A-8C graphically illustrate aspects of method 100. FIG. 8A is a schematic illustration of MCD 28 with some smaller first magnetic chips 60A accumulated in cavity 40 formed in magnet 36 of MCD 28. During operation, MCD 28 may be at least partially immersed in lubrication fluid 26 which may be flowing past MCD 28. Some lubricating fluid 26 may enter and exit gap 38 and cavity 40 formed in magnet 36. Magnetic chips that are suspended and/or carried by lubrication fluid 26 may be attracted and retained by MCD 28 due to the presence of magnet 36. The situation represented in FIG. 8A shows smaller first magnetic chips 60A that have entered cavity 40 via gap 38 and that are retained inside of cavity 40. A majority or substantially all of first magnetic chips 60A may be relatively fine ferromagnetic debris/particles that may normally be expected during an initial (break-in) period of operation of engine 10. First magnetic chips 60A may be made from metallic and electrically conductive material(s). The scenario of FIG. 8A shows first magnetic chips 60A entirely disposed in cavity 40 and outside of gap 38 so as not to electrically bridge gap 38. Since the collection of first magnetic chips 60A in cavity 40 of MCD 28 is not indicative of a developing or impending mechanical problem, no nuisance magnetic chip detection signal 56 is caused to be generated.

FIG. 8B is a schematic illustration of MCD 28 with first magnetic chips 60A accumulated in cavity 40 and also second magnetic chips 60B accumulated in gap 38. The scenario shown in FIG. 8B illustrates a situation where an amount of smaller magnetic chips 60A, 60B collected by MCD 28 is beyond what would be expected during operation in a typical initial (break-in) period of operation of engine 10. Such quantity of magnetic chips 60A, 60B may be indicative of a developing or impending mechanical problem. In this case, a portion of cavity 40 has been completely filled by first magnetic chips 60A and a quantity of second magnetic chips 60B is overflowing radially outwardly into gap 38. The presence of second magnetic chips 60B in gap 38 may cause electric bridging of first and second terminals 32, 34 and cause a legitimate magnetic chip detection signal 56 to be generated. The presence of cavity 40 allows for the accumulation of an amount of smaller magnetic chips 60A before triggering magnetic chip detection signal 56.

FIG. 8C is a schematic illustration of MCD 28 with smaller first magnetic chips 60A accumulated in cavity 40 and a larger second magnetic chips 60B electrically bridging first and second terminals 32, 34 across gap 38. The scenario shown in FIG. 8C illustrates a situation where an expected amount of smaller first magnetic chips 60A are collected in cavity 40 (i.e., outside of gap 38) and one or more larger second magnetic chips 60B are also collected by MCD 28. In this situation, first magnetic chips 60A do not cause magnetic chip detection signal 56 to be generated but second magnetic chips 60B provide an electric bridge between first and second terminals 32, 34 and thereby cause magnetic chip detection signal 56 to be generated despite being disposed outside of gap 38. Since the collection of second magnetic chips 60B of such large size may be indicative of a developing or impending mechanical problem, the magnetic chip detection signal 56 may be legitimate.

The specific dimensions of various features such as gap 38 and cavity 40 of MCD 28 may be selected based on an amount and characteristics (e.g., target size) of acceptable and relatively harmless first magnetic chips 60A expected to be collected during normal operation of engine 10 and also an amount and characteristics (e.g., target size) of relatively worrisome second magnetic chips 60B expected to be collected to indicate a developing or impending mechanical problem. Accordingly, features of MCD 28 may allow for the collection of smaller first magnetic chips 60A without triggering nuisance chips detections while also allowing gap 38 to be sized to detect second magnetic chips 60B of target amounts and/or sizes.

Maintenance may be required after a magnetic chip detection. Such maintenance may include troubleshooting and other task(s) required to remedy the developing or impending mechanical problem. Such maintenance may also include accessing MCD 28 to clean MCD 28 by removing magnetic chips 60A and 60B accumulated on the MCD 28.

The embodiments described in this document provide non-limiting examples of possible implementations of the present technology. Upon review of the present disclosure, a person of ordinary skill in the art will recognize that changes may be made to the embodiments described herein without departing from the scope of the present technology. Yet further modifications could be implemented by a person of ordinary skill in the art in view of the present disclosure, which modifications would be within the scope of the present technology.

What is claimed is:

1. A magnetic chip detector comprising:
   a first electric terminal;
   a second electric terminal spaced apart from the first electric terminal to define a gap therebetween, the gap having a width between the first and second electric terminals and a depth between a first side and a second side of the gap, the first side of the gap defining an opening for establishing fluid communication between the gap and an ambient environment; and
   a magnet disposed outside of the gap and adjacent the second side of the gap, the magnet including a recess defining a cavity in fluid communication with the gap to collect one or more magnetic chips that have entered the gap via the opening.

2. The magnetic chip detector of claim 1, wherein the gap and the cavity extend substantially completely around an axis.

3. The magnetic chip detector of claim 2, wherein the first and second electric terminals are axially spaced apart relative to the axis.

4. The magnetic chip detector of claim 3, wherein:
   the cavity is in substantial axial alignment with the gap; and
   the cavity is adjacent the gap.

5. The magnetic chip detector of claim 4, wherein
   a width of the cavity is substantially equal to the width of the gap.

6. The magnetic chip detector of claim 1, wherein:
   the first electric terminal defines a first receptacle in which a first portion of the magnet is received; and
   the second electric terminal defines a second receptacle in which a second portion of the magnet is received.

7. The magnetic chip detector of claim 1, wherein the cavity has a substantially U-shaped cross-sectional profile.

8. The magnetic chip detector of claim 1, wherein the cavity is adjacent the second side of the gap.

9. The magnetic chip detector of claim 2, wherein the first and second electric terminals are radially spaced apart relative to the axis.

10. The magnetic chip detector of claim 9, wherein:
    the cavity is in substantial radial alignment with the gap; and
    the cavity is adjacent the gap.

11. The magnetic chip detector of claim 1, wherein
    a width of the cavity is substantially equal to the width of the gap.

12. An aircraft engine comprising:
    a lubrication system for distributing lubrication fluid to one or more lubrication loads; and
    a magnetic chip detector immersed in the lubrication fluid, the magnetic chip detector comprising:
    a first electric terminal;
    a second electric terminal spaced apart from the first electric terminal to define a gap therebetween, the gap having a width between the first and second electric terminals and a depth between a first side and a second side of the gap, the first side of the gap defining an opening for establishing fluid communication between the gap and an ambient environment; and
    a magnet disposed outside of the gap, the magnet including a cavity formed therein, the cavity being disposed adjacent the second side of the gap and in fluid communication with the gap via the second side of the gap.

13. The aircraft engine of claim 12, wherein the gap and the cavity extend substantially completely around an axis.

14. The aircraft engine of claim 13, wherein the first and second electric terminals are axially spaced apart relative to the axis.

15. The magnetic chip detector of claim 13, wherein the first and second electric terminals are radially spaced apart relative to the axis.

16. The magnetic chip detector of claim 12, wherein a width of the cavity is substantially equal to the width of the gap.

17. A method of detecting one or more magnetic chips in a lubrication fluid of an engine using a magnetic chip detector including: a first electric terminal and a second electric terminal defining a gap therebetween; and a magnet including a magnet cavity adjacent the gap, the method comprising:
    receiving the lubrication fluid in the gap and in the magnet cavity;
    collecting one or more first magnetic chips inside the magnet cavity without generating a magnetic chip detection signal;
    collecting one or more second magnetic chips at the magnetic chip detector; and
    after collecting the one or more second magnetic chips at the magnetic chip detector, generating the magnetic chip detection signal.

18. The method of claim 17, comprising collecting the one or more second magnetic chips inside the gap.

19. The method of claim 17, comprising collecting the one or more second magnetic chips outside the gap.

20. The method of claim 17, wherein the one or more first magnetic chips are smaller than the one or more second magnetic chips.

* * * * *